United States Patent [19]

Alas et al.

[11] Patent Number: 5,600,013
[45] Date of Patent: Feb. 4, 1997

[54] PREPARATION OF CYCLIC KETONES

[75] Inventors: Michel Alas, Melle; Michel Crochemore, Chaponost, both of France

[73] Assignee: Rhone-Poulenc Chimie, Courbevoie Cedex, France

[21] Appl. No.: 539,041

[22] Filed: Oct. 4, 1995

Related U.S. Application Data

[63] Continuation of Ser. No. 251,271, May 31, 1994, abandoned.

[30] Foreign Application Priority Data

May 28, 1993 [FR] France .................. 93 06477

[51] Int. Cl.⁶ ............................. C07C 45/45
[52] U.S. Cl. .............. 568/355; 568/319; 568/397
[58] Field of Search .................. 568/355, 319, 568/397

[56] References Cited

U.S. PATENT DOCUMENTS

| 3,454,619 | 7/1969 | Hayes | 568/355 |
| 3,468,956 | 9/1969 | Mead | 568/355 |
| 5,001,273 | 3/1991 | Kline-Homann | 568/397 |

FOREIGN PATENT DOCUMENTS

| 0266687 | 5/1988 | European Pat. Off. | 568/355 |
| 0306873 | 3/1989 | European Pat. Off. | 568/355 |

*Primary Examiner*—James H. Reamer
*Attorney, Agent, or Firm*—Burns, Doane, Swecker & Mathis, L.L.P.

[57] ABSTRACT

Cyclic ketones, notably cyclopentanone and 2,2-dimethylcyclopentanone, are simply, economically and efficiently prepared, even on an industrial scale, by decarboxylating/cyclizing a dicarboxylic acid, in liquid phase, in the presence of a catalytically effective amount of a condensed or uncondensed neutral phosphate.

40 Claims, No Drawings

PREPARATION OF CYCLIC KETONES

CROSS-REFERENCE TO COMPANION APPLICATION

This application is a continuation of application Ser. No. 08/251,271, filed May 31, 1994 now abandoned.

BACKGROUND OF THE INVENTION

1. Field of the Invention

The present invention relates to the preparation of cyclic ketones, and, more especially, to the preparation of cyclic ketones from dicarboxylic acids.

The present invention more particularly relates to the preparation of cyclopentanone from adipic acid and 2,2-dimethylcyclopentanone from 2,2dimethyladipic acid.

2. Description of the Prior Art

GB-A-615,543 describes the preparation of cyclopentanone by heating adipic acid in the presence of manganese carbonate or oxide. The yield obtained in respect of cyclopentanone, when the cyclization reaction is carried out at 280° C., is excellent, on the order of 90%. However, this process is not completely satisfactory, as it is not possible to increase the level of cyclopentanone productivity. Indeed, to maintain the aforenoted levels of yield, it is necessary to limit the feedstream flow rates of adipic acid to about 0.7 kg/h per kilogram of catalyst. The feedstream flow rate could be increased by raising the reaction temperature.

Although the temperature indicated in GB-A-615,543 is said to range from 280° C. to 350° C., it is very difficult from an industrial standpoint to maintain a temperature of higher than 320° C. without using complex apparatus or special, expensive heat transfer fluids. In addition, it is very difficult, if not impossible, to maintain such a temperature homogeneous in the viscous medium which is constituted by the liquid adipic acid and the manganese-based catalyst. Too, other than the difficulties indicated above, risks are presented of the deposit of polymeric substrates on the reactor walls ("lining") which are difficult to remove.

Another process for the preparation of cyclopentanone via cyclization of adipic acid, in the presence of a magnesium oxide catalyst, is described in U.S. Pat. No. 2,612,524. This particular process also requires a high temperature, ranging from 300° C. to 350° C.

SUMMARY OF THE INVENTION

Accordingly, a major object of the present invention is the provision of an improved high-productivity process for the preparation of cyclic ketones that can simply and economically be carried out on an industrial scale and which does not require any sophisticated apparatus.

Briefly, the present invention features a process for the preparation of cyclic ketones, by decarboxylation and cyclization of a dicarboxylic acid having the following formula (I):

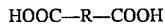

HOOC—R—COOH     (I)

in which R is a substituted or unsubstituted alkylene radical including a straight chain of atoms in sufficient number to form the desired ketonic ring member, said decarboxylation/cyclization reaction being carried out in the liquid phase, in the presence of a catalytically effective amount of a neutral condensed or uncondensed phosphate.

By the term "neural phosphate" is intended any compound of phosphorus derived from orthophosphoric acid and in which the protons (hydrogen atoms) are substituted by a metallic, ammonium or other cation.

DETAILED DESCRIPTION OF BEST MODE AND PREFERRED EMBODIMENTS OF THE INVENTION

More particularly according to the present invention, it has now surprisingly been found that the subject neutral phosphate catalysts, and preferably sodium phosphate, are more active than the manganese-based catalysts. It is thus possible to increase the feed rate of dicarboxylic acid and especially adipic acid in a ratio of from 1 to 4.

According to the process of the invention, a dicarboxylic acid is used which corresponds to formula (I) in which R is a substituted or unsubstituted alkylene radical including a straight chain of atoms in sufficient number to form the desired ketonic ring member.

Generally, the radical R comprises a straight chain of from 2 to 10 atoms, preferably from 2 to 7 atoms, and even more preferably from 4 to 5 atoms. It typically comprises a chain of carbon atoms, but the invention does not exclude the hydrocarbon chain being interrupted by a heteroatom, in particular nitrogen, oxygen or sulfur.

As indicated above, the radical R may be substituted, namely, the hydrogen atoms of the hydrocarbon chain may be replaced by a substituent or functional group. Any substituents may be present so long as they do not interfere with the decarboxylation/cyclization reaction. In particular, the hydrocarbon chain may be substituted by side or branched chains, preferably by alkyl radicals generally having from 1 to 4 carbon atoms. The branched chains are typically situated on one or the two carbon atoms in the α- or β-position to the carboxylic groups.

In general, the radical R has a total number of carbon atoms which can vary broadly from 2 carbon atoms to a number as high as 40 carbon atoms when substituents are present and said radical comprises a straight chain of from 2 to 10 atoms which constitute the ring member thus formed.

In the formula (I), R is preferably a branched or straight alkylene radical, more preferably a branched or straight alkylene radical having from 2 to 20 carbon atoms.

The dicarboxylic acids of general formula (I) in which the aliphatic radical R is a branched or straight alkylene radical having from 2 to 12 carbon atoms and which comprises a straight chain of from 2 to 8 carbon atoms between the two COOH groups are very well suited for carrying out the process of the invention.

The preferred radical R comprises a straight chain of from 4 to 5 carbon atoms between the two COOH groups.

In the process of the invention, a dicarboxylic acid of formula (I) can be used in which R is a branched or straight alkylene radical wherein two adjacent carbon atoms can form a ring member.

By the term "ring" or "ring member" is intended a saturated or aromatic carbocyclic or heterocyclic ring.

Exemplary such rings are cycloaliphatic, aromatic or heterocyclic rings, in particular cycloalkyl rings having 6 carbon atoms in the ring, or benzene rings, such rings themselves optionally bearing one or more substituents, as long as they do not interfere with the decarboxylation/cyclization reaction.

Exemplary such radicals R include, e.g., the following:

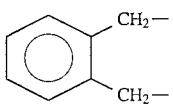 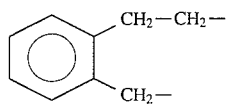

Among the carboxylic acids of formula (I) which are suitable according to the present invention, particularly representative are the following dicarboxylic acids:

Adipic acid,
2-Methyladipic acid,
3-Methyladipic acid,
4-Methyladipic acid,
5-Methyladipic acid,
2,2-Dimethyladipic acid,
3,3-Dimethyladipic acid,
2,2,5-Trimethyladipic acid,
2,5-Dimethyladipic acid,
Pimelic (heptanedioic) acid,
2-Methylpimelic acid,
2,2-Dimethylpimelic acid,
3,3-Dimethylpimelic acid,
2,5-Dimethylpimelic acid,
2,2,5-Trimethylpimelic acid,
Azelaic acid,
Sebacic acid, and
1,2-Phenylenediacetic acid In accordance with the process of the invention, the cyclization of the dicarboxylic acid is carried out in the presence of a neutral phosphate catalyst.

According to this invention, the phosphate is employed in any form. However, for reasons of economy, it is preferred to use those phosphates that are readily commercially available.

The orthophosphates are preferably used, but condensed phosphates can also be employed, namely, phosphates containing more than one phosphorus atom. These are formed/constituted by a chain or backbone of tetrahedric units $PO_4$ which are linked together via oxygen atoms. Such units may constitute, for example, straight phosphate chains containing from 2 to 10 phosphorus atoms. Exemplary thereof are anions respectively having 2 or 3 phosphorus atoms, such as the pyrophosphate $P_4O_7^{2-}$ or tripolyphosphate $P_3O_{10}^{5-}$.

As regards the counterion, it may be of any nature whatsoever. It may comprise a metallic element or, more particularly, an element from Groups 1a, 2a or 3b of the Periodic Table of elements, or an ammonium cation.

By "Periodic Table" is intended that published in the *Bulletin de la Société Chimique de France*, No. 1 (1966).

The catalyst is thus a metallic or ammonium phosphate. Mixtures of phosphates, or mixed salts thereof, can also be used.

The following phosphates are very well suited for carrying out the process of the present invention:

Sodium phosphate $Na_3PO_4$
Potassium phosphate,
Sodium pyrophosphate $Na_2P_4O_7$
Potassium pyrophosphate,
Aluminum phosphate,
Ammonium phosphate,
Silver phosphate,
Barium phosphate,
Calcium phosphate,
Chromium phosphate,
Cobalt phosphate,
Copper phosphate,
Double magnesium and ammonium phosphate,
Iron phosphate,
Ferrous phosphate,
Lithium phosphate,
Magnesium phosphate,
Manganese phosphate,
Potassium phosphate,
Zinc phosphate,
Calcium pyrophosphate,
Copper pyrophosphate,
Zinc pyrophosphate,
Sodium pentapolyphosphate $Na_7P_6O_{16}$,
Sodium tripolyphosphate $Na_5P_3O_{10}$, and
Potassium tripolyphosphate $K_5P_3O_{10}$.

The phosphate catalysts of the invention may be employed either in anhydrous or hydrated form.

Among the catalysts indicated above, the sodium or potassium phosphates, pyrophosphates, tripolyphosphates or pentapolyphosphates are particularly preferred.

The catalysts of the invention, being active at low temperature, the subject process is carried out in liquid phase, preferably in the presence of a reaction solvent.

The dicarboxylic acid can itself be used as a reaction solvent, but preferably an organic solvent is used as a thermal transfer flux.

A number of requirements govern the selection of the organic solvent.

It must be stable under the reaction conditions and inert with respect to the starting material carboxylic acid and the cyclic ketone final product.

It must have a high boiling point, preferably from 200° C. to 500° C.

Particularly exemplary solvents which are suitable according to the present invention include the following:

(a) aliphatic and/or aromatic hydrocarbons and more particularly paraffins such as, in particular, decane, undecane, dodecane or tetradecane; aromatic hydrocarbons such as, in particular, xylenes, cumene, and petroleum cuts comprising a mixture of alkyl benzenes, in particular cuts of the Solvesso® type, (b) heavy esters of inorganic acids (for example tricresyl phosphate) or carboxylic acids (for example octyl phthalate), (c) ethers and more particularly aromatic ethers, such as biphenyl oxide and/or benzyl oxide, and (d) paraffinic and/or naphthenic oils, petroleum distillation residues.

A mixture of organic solvents can also be employed.

The process of the invention therefore entails use of the starting material dicarboxylic acid, the catalyst for the reaction and the organic solvent.

The concentration of dicarboxylic acid in the reaction mass may vary widely. In general, the dicarboxylic acid constitutes from 20% to 50% of the weight of the reaction mass/medium.

The amount of catalyst used, expressed in terms of the number of atoms of metallic cation per 100 moles of dicarboxylic acid, advantageously ranges from 0.1% to 20%, preferably from 1% to 10%.

From a practical point of view, when the process of the invention is carried out discontinuously, the procedure generally comprises first introducing the reaction solvent and the catalyst, followed by addition of the dicarboxylic acid, preferably in premelted state (molten).

The process of the invention can be carried out both discontinuously and continuously. In the former event, only the dicarboxylic acid is supplied.

The feedstream dicarboxylic acid flow rate can vary widely, e.g., from 0.1 to 4.0 kg/hour per kilogram of catalyst introduced. It preferably ranges from 0.5 to 1.0 kg/hour and per kilogram of catalyst.

The process of the invention is advantageously carried out at a temperature below 300° C., preferably ranging from 200° C. to 300° C. and more preferably from 250° C. to 290°C.

It is generally carried out at atmospheric pressure, but can also be conducted under a reduced pressure of, for example, from 50 to 760 mm of mercury.

A preferred embodiment of the process of the invention comprises the elimination by distillation, as they are formed, of the cyclic ketone, the carbon dioxide gas and the water.

At the end of the reaction, the cyclic ketone is recovered from the distillate using conventional procedures, in particular by settling or crystallization.

The process of the invention is well suited for the preparation of cyclopentanone, 2,2-dimethylcyclopentanone and cyclohexanone.

In order to further illustrate the present invention and the advantages thereof, the following specific examples are given, it being understood that same are intended only as illustrative and in nowise limitative.

In said examples to follow, the following abbreviations are employed:

RAH=ratio of hourly feed of adipic acid with respect to the catalyst $$RAH = \frac{\text{hourly charge of adipic acid (by weight)}}{\text{charge of catalyst (by weight)}}$$

$$TT = \frac{\text{number of moles of adipic acid converted}}{\text{number of moles of adipic acid introduced}} \%$$

The operating procedure employed in all Examples is more fully described below.

The apparatus used was always the same. It was a 1,000 ml glass balloon flask provided with a magnetic agitation means and surmounted by a Rashig column measuring 20 mm in diameter and 100 mm in height. The column head comprised a pouring funnel heated with a hot air jet for supplying the adipic acid which was melted beforehand.

The reaction solvent and the catalyst were introduced and then the molten adipic acid was added.

Continuous distillation of the cyclopentanone was effected at 130° C. at the column head, feeding the adipic acid onto the solvent/catalyst mixture which was maintained at a temperature of 250°C.

The different amounts of adipic acid and catalyst which were introduced are reported in Table I which follows.

The nature of the reaction solvent is also reported in Table I. The volume of solvent was 500 ml.

At the end of the reaction, a distillate was recovered, comprising water and the cyclopentanone. The water was separated from the cyclopentanone by saturating the distillate with sodium chloride. The cyclopentanone was analyzed by gaseous phase chromatography.

As regards the distillation bottoms, it was extracted with 3×600 ml of a mixture of water and sodium hydroxide (60/40 by volume). The total volume was adjusted to 2,000 ml. 10 ml were drawn off, adjusted to 100 ml with a mixture of water/sodium hydroxide (15/85 by volume) containing 0.035% of phosphoric acid. The unconverted adipic acid was analyzed by high-performance liquid chromatography.

The tests were carried out in accordance with the operating procedure described above.

All of the operating conditions and results obtained are reported in the following Table I:

TABLE I

| Example | Solvent Nature | Solvent Volume | Catalyst Nature | Catalyst Weight | Adipic acid introduced Total (g) | Adipic acid introduced /h | RAH | Time (h) | Acid remaining (g) | Cyclopentanone Weight (g) | RT (%) |
|---|---|---|---|---|---|---|---|---|---|---|---|
| 1 | Biphenyl oxide | 500 | $Na_3PO_4.H_2O$ | 8.5 | 475 | 19.8 | 2.3 | 24 | 90 | 204 | 92 |
| 2 | Benzyl oxide | 500 | $FePO_4.2H_2O$ | 9.5 | 300 | 18.75 | 2.0 | 16 | 80 | 83 | 66 |
| 3 | Biphenyl oxide | 450 | $BiPO_4$ | 8 | 217.5 | 27.2 | 3.4 | 8 | 52 | 56.6 | 59.5 |
|   | Benzyl oxide | 50 |   |   |   |   |   |   |   |   |   |
| 4 | Biphenyl oxide | 500 | $LiPO_4$ | 9 | 500 | 20.8 | 2.3 | 24 | 45 | 246 | 94 |

-continued $$RT = \frac{\text{number of moles of cyclopentanone formed}}{\text{number of moles of adipic acid converted}} \%$$

EXAMPLES 1 TO 4

The following Examples were carried out employing a continuous mode of operation.

EXAMPLES 5 TO 9

The operating procedure described below was employed.

A series of tests entailing a discontinuous mode of operation was carried out.

The following materials were introduced into a 250 ml reactor provided with a magnetic agitation means and surmounted by a packed Multiknit column measuring 20 mm in diameter and 100 m in height, heat-insulated and fitted with a column head:

(i) the reaction solvent, which was biphenyl oxide, in a proportion of 140 ml, (ii) the catalyst whose nature is reported in Table II, in a proportion of 0.01 mole, and, (iii) the molten adipic acid, namely, 0.2 mole (29.2 g).

The reaction mixture was placed under light reflux such that the vapors did not extend beyond the bottom of the column.

The cyclopentanone formed was distilled at the column head at a temperature equal to 130° C. until exhaustion occurred.

The duration of the operation was 8 hours.

The results obtained are reported in Table II:

TABLE II

| | Catalyst | | | |
|---|---|---|---|---|
| Example | Nature | Weight (g) | TT (%) | RT (%) |
| 5 | $Na_3PO_4.H_2O$ | 1.8 | 71 | 90 |
| 6 | $Fe_3(PO_4)_2.8H_2O$ | 5.0 | 82 | 93 |
| 7 | $Mn_3(PO_4)_2.3H_2O$ | 4.1 | 59 | 67 |
| 8 | $Pb_3(PO_4)_2$ | 8.1 | 64 | 72 |
| 9 | $K_3PO_4.2H_2O$ | 2.5 | 70 | 85 |

EXAMPLE 10

5 g of 2,2-dimethyladipic acid were heated in the presence of 1.1 g of sodium phosphate $Na_3PO_4.H_2O$ and 17 ml of biphenyl oxide were added at 225° C. over 1 hour, 35 min.

The distillate, cooled to about 0° C., comprised two phases. After eliminating the water by absorption on sodium sulfate, the 2,2-dimethylcyclopentanone obtained was determined by gaseous phase chromatography.

The distillation bottoms was washed with an aqueous basic solution (3×100 ml of an aqueous solution of sodium hydroxide 1 N) to extract the unconverted acid.

Quantitative determination by high-performance liquid chromatography provided the following results:

(a) $TT_{adipic\ acid}=85\%$, (b) $RT_{2,2\text{-}dimethylcyclopentanone}=90\%$.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a cyclic ketone, comprising decarboxylating/cyclizing a dicarboxylic acid in the presence of a catalytically effective amount of a condensed or uncondensed neutral phosphate.

2. The process as defined by claim 1, said dicarboxylic acid having the formula:

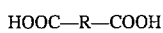  (I)

in which R is a substituted or unsubstituted alkylene radical including a straight chain of atoms in sufficient number to form the desired ketonic ring member.

3. The process as defined by claim 2, wherein formula (I), the radical R comprises a straight chain of from 2 to 10 atoms.

4. The process as defined by claim 3, wherein formula (I), the radical R comprises a straight chain of 4 or 5 atoms.

5. The process as defined by claim 2, wherein formula (I), the radical R is substituted.

6. The process as defined by claim 5, wherein formula (I), the radical R comprises at least one lower alkyl branch substituent.

7. The process as defined by claim 6, wherein formula (I), said at least one branch substituent is situated on one or the two carbon atoms in the α- or β-position to the carboxylic groups.

8. The process as defined by claim 3, wherein formula (I), the radical R has from 2 to 40 carbon atoms.

9. The process as defined by claim 8, wherein formula (I), the radical R has from 2 to 12 carbon atoms.

10. The process as defined by claim 1, said dicarboxylic acid comprising adipic acid, 2-methyl adipic acid, 3-methyladipic acid, 4-methyladipic acid, 5methyladipic acid, 2,2-dimethyladipic acid, 3,3-dimethyladipic acid, 2,2,5-trimethyladipic acid, 2,5-dimethyladipic acid, pimelic (heptanedioic) acid, 2-methylpimelic acid, 2,2-dimethylpimelic acid, 3,3-dimethylpimelic acid, 2,5-dimethylpimelic acid, 2,2,5-trimethylpimelic acid, azelaic acid, sebacic acid, or 1,2-phenylenediacetic acid.

11. The process as defined by claim 10, said dicarboxylic acid comprising adipic acid or 2,2-dimethyladipic acid.

12. The process as defined by claim 1, said active catalyst comprising a phosphate, pyrophosphate or polyphosphate, either in anhydrous or hydrated state.

13. The process as defined by claim 12, the counterion of said phosphate, pyrophosphate or polyphosphate comprising a metallic or ammonium cation.

14. The process as defined by claim 13, the counterion of said phosphate, pyrophosphate or polyphosphate comprising a cation of an element of Group 1a, 2a or 3b of the Periodic Table.

15. The process as defined by claim 12, said active catalyst comprising a pyrophosphate or polyphosphate.

16. The process as defined by claim 12, said active catalyst comprising a sodium or potassium phosphate, pyrophosphate, tripolyphosphate or pentapolyphosphate.

17. The process as defined by claim 12, said active catalyst comprising sodium phosphate $Na_3PO_4$, potassium phosphate, sodium pyrophosphate $Na_2P_4O_7$, potassium pyrophosphate, aluminum phosphate, ammonium phosphate, silver phosphate, barium phosphate, calcium phosphate, chromium phosphate, cobalt phosphate, copper phosphate, double magnesium and ammonium phosphate, iron phosphate, ferrous phosphate, lithium phosphate, magnesium phosphate, manganese phosphate, potassium phosphate, zinc phosphate, calcium pyrophosphate, copper pyrophosphate, zinc pyrophosphate, sodium pentapolyphosphate $Na_7P_6O_{16}$, sodium tripolyphosphate $Na_5P_3O_{10}$, or potassium tripolyphosphate $K_5P_3O_{10}$.

18. The process as defined by claim 1, carried out in the presence of a reaction solvent.

19. The process as defined by claim 18, said reaction solvent comprising an aliphatic and/or aromatic hydrocarbon, a heavy ester of an inorganic or organic acid, an ether, a paraffinic and/or naphthenic oil, or a residue of petroleum distillation.

20. The process as defined by claim 1, wherein the concentration of dicarboxylic acid in the medium of reaction ranges from 20% to 50% by weight thereof.

21. The process as defined by claim 1, wherein the amount of said active catalyst, expressed as the number of atoms of metallic cation per 100 moles of said dicarboxylic acid, ranges from 0.1% to 20%.

22. The process as defined by claim 21, wherein the amount of active catalyst ranges from 1% to 10%.

23. The process as defined by claim 18, comprising introducing said reaction solvent and said active catalyst into a reaction zone and then adding said dicarboxylic acid thereto.

24. The process as defined by claim 23, the dicarboxylic acid added being in molten state.

25. The process as defined by claim 1, comprising reacting from 0.1 to 4.0 kg/hour of said dicarboxylic acid per kilogram of active catalyst.

26. The process as defined by claim 25, comprising reacting from 0.5 to 1.0 kg/hour of said dicarboxylic acid per kilogram of active catalyst.

27. The process as defined by claim 1, carried out at a temperature ranging from 200° to 300° C.

28. The process as defined by claim 1, comprising the preparation of cyclopentanone.

29. The process as defined by claim 1, comprising the preparation of 2,2-dimethylcyclopentanone.

30. The process as defined by claim 1, comprising the preparation of cyclohexanone.

31. The process according to claim 2, wherein the aliphatic radical R in the dicarboxylic acid of formula (I), comprises a straight chain alkylene radical having from 2 to 8 carbon atoms between the two COOH groups.

32. The process according to claim 31, wherein the straight chain alkylene radical comprises 4 or 5 carbon atoms between the two COOH groups.

33. The process according to claim 18, wherein the reaction solvent is a paraffin selected from the group consisting of decane, undecane, dodecane and tetradecane.

34. The process of claim 19, wherein the aromatic hydrocarbon is selected from the group consisting of xylenes, cumene and petroleum cuts produced by a mixture of alkyl benzenes.

35. The process of claim 34, wherein said petroleum cut is of the Solvesso® type.

36. The process of claim 18, wherein the reaction solvent comprises a heavy ester of a mineral acid or a carboxylic acid.

37. The process of claim 36, wherein said heavy ester of a mineral acid comprises tricresyl phosphate.

38. The process of claim 37, wherein the heavy ester of a carboxylic acid is octyl phthalate.

39. The process of claim 19, wherein the ether is an aromatic ether.

40. The process of claim 39, wherein said aromatic ether comprises biphenyl oxide and/or benzyl oxide.

* * * * *